(12) United States Patent
O'Lenick

(10) Patent No.: US 7,875,263 B1
(45) Date of Patent: Jan. 25, 2011

(54) POLYMERIC STRUCTURED GELS

(76) Inventor: Kevin O'Lenick, 2170 Luke Edwards Rd., Dacula, GA (US) 30019

( * ) Notice: Subject to any disclaimer, the term of this patent is extended or adjusted under 35 U.S.C. 154(b) by 425 days.

(21) Appl. No.: 11/708,079

(22) Filed: Feb. 20, 2007

Related U.S. Application Data

(60) Provisional application No. 60/877,109, filed on Dec. 26, 2006.

(51) Int. Cl.
*A61K 47/44* (2006.01)
*A61K 8/02* (2006.01)
*A61K 8/00* (2006.01)
*C08G 77/04* (2006.01)

(52) U.S. Cl. .................. 424/59; 424/401; 514/786; 528/10

(58) Field of Classification Search .................. None
See application file for complete search history.

(56) References Cited

U.S. PATENT DOCUMENTS

| | | | | |
|---|---|---|---|---|
| 4,065,417 | A | * 12/1977 | Wong et al. | .................. 524/35 |
| 5,073,573 | A | * 12/1991 | Martin et al. | ................ 424/401 |
| 5,623,017 | A | 4/1997 | Hill | |
| 6,001,339 | A | * 12/1999 | Finel et al. | ............... 424/70.12 |
| 6,126,951 | A | * 10/2000 | Fogel | ......................... 424/401 |
| 2002/0058014 | A1 | * 5/2002 | Gers-Barlag et al. | .......... 424/59 |
| 2006/0008426 | A1 | * 1/2006 | Doring et al. | ................. 424/59 |

FOREIGN PATENT DOCUMENTS

| | | | |
|---|---|---|---|
| JP | H10-29916 | * | 2/1998 |
| JP | 11092694 | * | 4/1999 |
| JP | 2002-264484 | * | 9/2002 |

OTHER PUBLICATIONS

Tricaprylin MSDS. http://www.sciencelab.com/xMSDS-Tricaprylin-9925305. Accessed Jul. 23, 2009.*
Resin. http://wordnetweb.princeton.edu/perl/webwn?s=resin. Accessed Oct. 22, 2008.*
Enhancing the Feel of Vegetable Oils With Siuwne—Girboux et al Cosmetics & Toiletries vol. 123 No. 7 Jul. 2008 p. 49,50,52,53, 54&56 Allnred Publishing Carol Stream IL USA.

* cited by examiner

*Primary Examiner*—Andrew D Kosar
*Assistant Examiner*—Lori Mattison

(57) ABSTRACT

The present invention is directed to a gel composition which comprises an specific solid alkyl silicone polymers combined with specific liquid esters selected from the group consisting of glyceryl esters, trimethylolpropane esters, and pentaerythritol esters. The invention is also directed to a process for providing emolliency to the skin by applying the compositions of the present invention. Finally, the invention is also directed to application of sun screen actives, hydroxy acids, antioxidants, flavonoids, tocopherol, vitamins and the like to the skin in gelled form.

19 Claims, No Drawings

POLYMERIC STRUCTURED GELS

RELATED APPLICATIONS

This application claims priority to and benefit of U.S. Provisional Application No. 60/877,109 filed Dec. 26, 2006, the disclosure of which is incorporated herein for all purposes.

FIELD OF THE INVENTION

The present invention is directed to a gel composition which comprises an specific solid alkyl silicone polymers combined with specific liquid esters selected from the group consisting of glyceryl esters, trimethylolpropane esters, and pentaerythritol esters.

The invention is also directed to a process for providing emolliency to the skin by applying the compositions of the present invention.

The invention is also directed to application of sun screen actives, hydroxy acids, antioxidants, flavonoids, tocopherol, vitamins and the like to the skin in gelled form.

BACKGROUND OF THE INVENTION

There is a long felt need for gelled products in the personal care market. Gels allow for application to the skin of cosmetically elegant materials that provide benefit to the skin.

One example of the use of gels is the jellification of cyclomethicone with a combination of water and water-soluble dimethicone copolyol materials. The gel is used to deliver antiperspirant actives to the skin in a dry feeling system. Typical of the technology is U.S. Pat. No. 5,623,017, issued Apr. 22, 1997 to Hill, entitled Clear silicone gels describes "a method of forming a thermodynamically stable transparent product by combining (i) water, (ii) a volatile cyclic methyl siloxane or volatile linear methyl siloxane; and (iii) a silicone polyether surfactant." This patent exemplifies the approach that has been taken to make gels of cyclomethicone for use in personal care products. The patent is related to thickening cyclomethicone, not esters with water (which is absent in the present invention), with an ethoxylated silicone. In short the art teaches that there is a long felt need to make gels in the personal care industry.

Those materials that are clear in the solvent generally define the concept of what is soluble. Sodium chloride is soluble in water. That is it is clear, but is also uniformly distributed in the solution. Unlike sodium chloride, which makes a uniform concentration solvent, materials that are bipolar are clear in water, but do not have uniform distribution in the solvent. The common example is sodium lauryl sulfate (SLS). SLS has a water-soluble sulfate group and an oil soluble lauryl portion (C12 hydrophobe). When SLS is added to water it is clear and consequently soluble. However, the molecule accumulates at the surface, lowering the surface tension. At a concentration called the CMC (critical micelle concentration) agglomerates form. SLS has an oil soluble and water-soluble group as shown below:

$CH_3(CH_2)_{11}$—$SO_4^-Na^+$

Oil Soluble|Water soluble

We have surprisingly found that in a way analogous to water based systems; ester based systems, into which alkyl silicones are introduced are soluble (form clear solutions) but at lower concentrations lower surface tension (from about 32 dynes/cm$^2$ to 22 dynes/cm$^2$) then above their cmc (critical micelle concentration) form micelles. In the past the phenomenon was thought to occur only in water based systems. The alkyl silicone is bipolar, (like SLS) but lacks a water-soluble group having instead an oil soluble alkyl group and an oil insoluble silicone group. Alkyl Silicones exist in two types as shown below:

Comb Products:

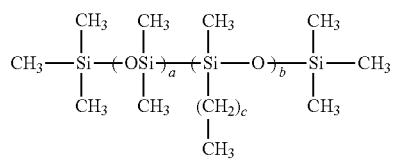

Terminal Products:

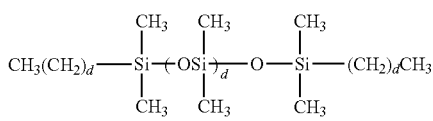

The selection of a proper alkyl silicone (that is one with a melting point of over 30° C., and combining it with specific liquid esters results in a gel that liquefies under pressure providing outstanding cosmetic aesthetics and delivery of a rande og oil soluble actives including sun screens.

By gel is meant a semi-solid material stabilized or set by a three-dimensional lattice system. Because one additive has a bipolar amphilic structure the molecules accumulate preferentially at the interface of two immiscible phases. If the concentration at the interface exceeds the critical micelle forming concentration (cmc), a colloidal surfactant solution is produced. With increasing concentration, or volume fraction of the internal phase, such a solution becomes a structured gel.

Bailey in U.S. Pat. No. 3,299,112 describes products formed from a ternary system of water, a silicone oil, and a silicone polyether. But in contrast to my invention, the products in Bailey are emulsions which are not clear; the ternary system of the '112 patent is not a gel; the silicone oil in Bailey is not a volatile cyclic VMS; and where Bailey does describe a linear silicone oil, it is not a volatile linear silicone oil.

The structured gels of the present invention are oil soluble esters that are modified to have unique skin spreadability properties. This provides particular value in the personal care arena. Specifically, the ester based structured gels are useful as a carrier in antiperspirants, pigmented products, skin care products, and the like since they spread rapidly and efficiently on the skin from a stiff gel providing emmoliency and a host of ester soluble additives including sun screen actives, hydroxy acids, antioxidants, flavonoids, tocopherol, vitamins and the like. The gels are very cosmetically appealing having a dry feel on the skin and provide a lubricious property which improve the properties of skin creams, skin care lotions, moisturizers, facial treatments such as acne or wrinkle removers, personal and facial cleansers, liquid soaps, bath oils, perfumes, colognes, sachets, sunscreens, pre-shave and after-shave lotions, shaving soaps, and shaving lathers. It can be used in hair shampoos, hair conditioners, hair sprays, mousses, permanents, depilatories, and cuticle coats, to enhance cosmetic elegance.

In cosmetics, the compositions of the present invention will function as a leveling and spreading agent for pigments in make-ups, color cosmetics, foundations, blushes, lipsticks, lip balms, eyeliners, mascaras, oil removers, color cosmetic removers, and powders. It is also useful as a delivery system for oil and water-soluble substances such as vitamins. When incorporated into sticks, other gels, lotions, aerosols, and roll-ons, the compositions of the present invention impart a silky-smooth feeling, an outstanding payout.

THE INVENTION

Objectives of the Invention

The object of present invention is to provide a structured gel composition comprising an specific solid alkyl silicone polymers combined with specific liquid esters selected from the group consisting of glyceryl esters, trimethylolpropane esters, and pentaerythritol esters.

Another objective of the present invention is a process for providing emolliency to the skin by applying the compositions of the present invention, The invention is also directed to application of sun-screen actives, hydroxy acids, antioxidants, flavonoids, tocopherol, vitamins and the like to the skin in gelled form.

Other objectives will become clear as one reads the disclosure.

All temperatures disclosed herein are degrees C., All percentages are percentages by weight, All patents referred to herein to the extent permitted are incorporated herein by reference.

SUMMARY OF THE INVENTION

The present invention is directed to a structured gel composition comprising (a) a solid alkyl silicone having a melting point of above 30° C., and (b) a liquid complex esters selected from the group consisting of glyceryl esters, trimethylolpropane esters an pentaerythritol esters. The liquid esters have melting points of below 25° C.

DETAILED DESCRIPTION OF THE INVENTION

The present invention is directed to a structured gel composition comprising (a) an alkyl dimethicone polymer selected from the group consisting of:

i. a comb branched alkyl dimethicone polymer conforming to the following structure;

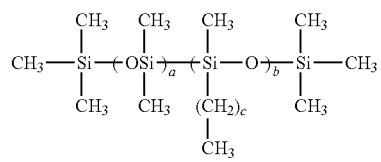

wherein:
a is an integer ranging from 0 to 200;
b is an integer ranging from 1 to 50;
c is an integer ranging from 17 to 35;

ii. a terminal alkyl dimethicone polymer conforming to the following structure;

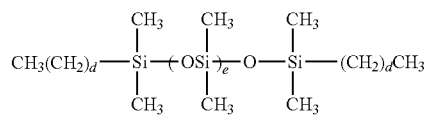

wherein:
d is an integer ranging from 17 to 35;
e in an integer ranging from 1 to 100;
and iii. mixtures thereof;
said alkyl dimethicone polymers having a melting point of above 30° C., and (b) a liquid complex esters §elected from the group consisting of i. glyceryl esters conforming to the following structure;

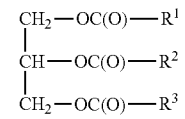

wherein;
$R^1$, $R^2$ and $R^3$ are independently selected from the group consisting of:
—$(CH_2)_e CH_3$;
$CH_3(CH_2)_7 CH=CH(CH_2)_7$—;
$CH_3$—$(CH_2)_4$—$CH=CH$—$CH_2$—$CH=CH$—$(CH_2)_7$— and mixtures thereof;
e is an integer ranging from 5 to 11;

ii. trimethylolpropane esters conforming to the following structure;

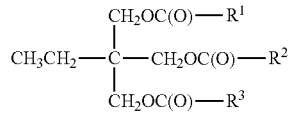

wherein;
$R^1$, $R^2$ and $R^3$ are independently selected from the group consisting of:
—$(CH_2)_e CH_3$;
$CH_3(CH_2)_7 CH=CH(CH_2)_7$—; $CH_3$—$(CH_2)_4$—$CH=CH$—$CH_2$—$CH=CH$—$(CH_2)_7$— and mixtures thereof;
e is an integer ranging from 6 to 12;
and iii. pentaerythritol esters conforming to the following structure;

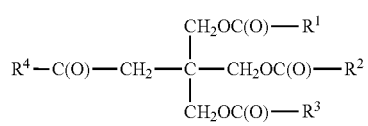

wherein;
R$^1$, R$^2$, R$^3$ and R$^4$ are independently selected from the group consisting of:
—(CH$_2$)$_e$CH$_3$;
CH$_3$(CH$_2$)$_7$CH=CH(CH$_2$)$_7$—; CH$_3$—(CH$_2$)$_4$—CH=CH—CH$_2$—CH=CH—(CH$_2$)$_7$— and mixtures thereof;
e is an integer ranging from 6 to 12;
iv. and mixtures thereof;
wherein said esters have melting points of below 25° C.

We have fund that when the "R" definitions are as shown the melting of the ester is as described and when the "c" and "e" values are as described, the alkyl silicones are solids as described. The components of the composition are added together and heated to 80° C. Upon which they become clear (solutions). Upon cooling gels form. The gles range from soft non-flowable solids to hard non-flowable solids. These gels liquefy under pressure of the finger, spread well no the skin and provide an excellent cosmetic feel. In instances where delivery is desired, the active is added. The actives include sun screen actives, hydroxy acids, antioxidants, flavonoids, tocopherol, vitamins and the like.

The present invention is also directed to a process for treating skin with a structured gel composition comprising contacting the skin with an effective conditioning concentration of a composition, which comprises;

(a) an alkyl dimethicone polymer selected from the group consisting of:
i. a comb branched alkyl dimethicone polymer conforming to the following structure;

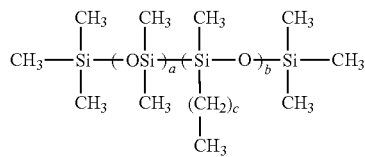

wherein:
a is an integer ranging from 0 to 200;
b is an integer ranging from 1 to 50;
c is an integer ranging from 17 to 35;
ii. a terminal alkyl dimethicone polymer conforming to the following structure;

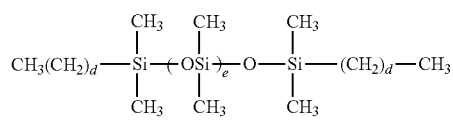

wherein:
d is an integer ranging from 17 to 35;
e in an integer ranging from 1 to 100;
and
iii. mixtures thereof;
said alkyl dimethicone polymers having a melting point of above 30° C., and (b) a liquid complex esters selected from the group consisting of
i. glyceryl esters conforming to the following structure;

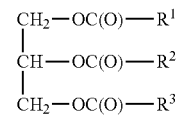

wherein;
R$^1$, R$^2$ and R$^3$ are independently selected from the group consisting of:
—(CH$_2$)$_e$CH$_3$;
CH$_3$(CH$_2$)$_7$CH=CH(CH$_2$)$_7$—;
CH$_3$—(CH$_2$)$_4$—CH=CH—CH$_2$—CH=CH—(CH$_2$)$_7$— and mixtures thereof;
e is an integer ranging from 5 to 11;
ii. trimethylolpropane esters conforming to the following structure

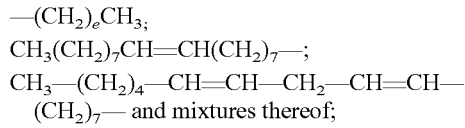

wherein;
R$^1$, R$^2$ and R$^3$ are independently selected from the group consisting of:
—(CH$_2$)$_e$CH$_3$;
CH$_3$(CH$_2$)$_7$CH=CH(CH$_2$)$_7$—;
CH$_3$—(CH$_2$)$_4$—CH=CH—CH$_2$—CH=CH—(CH$_2$)$_7$— and mixtures thereof;
e is an integer ranging from 6 to 12;
and
iii. pentaerythritol esters conforming to the following structure;

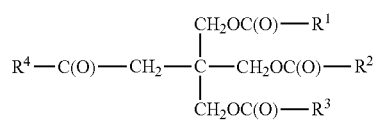

wherein;
R$^1$, R$^2$, R$^3$ and R$^4$ are independently selected from the group consisting of:
—(CH$_2$)$_e$CH$_3$;
CH$_3$(CH$_2$)$_7$CH=CH(CH$_2$)$_7$—;
CH$_3$—(CH$_2$)$_4$—CH=CH—CH$_2$—CH=CH—(CH$_2$)$_7$— and mixtures thereof;
e is an integer ranging from 6 to 12;
iv. and mixtures thereof;
wherein said esters have melting points of below 25° C.
and
(c) optionally sun screen actives, hydroxy acids, antioxidants, flavonoids, tocopherol, and vitamins.

Preferred Embodiments

In a preferred embodiment the alkyl dimethicone polymer is a comb branched alkyl dimethicone polymer conforming to the following structure;

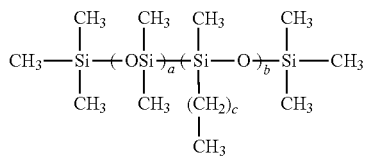

wherein:
a is an integer ranging from 0 to 200;
b is an integer ranging from 1 to 50;
c is an integer ranging from 17 to 35.

In another preferred embodiment the alkyl dimethicone polymer is a terminal alkyl dimethicone polymer conforming to the following structure;

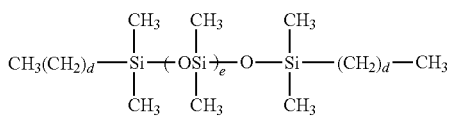

wherein:
d is an integer ranging from 17 to 35;
e in an integer ranging from 1 to 100;

In another preferred embodiment the alkyl dimethicone polymer is a mixture of a comb and terminal.

In a preferred embodiment the liquid complex esters is a glyceryl ester conforming to the following structure;

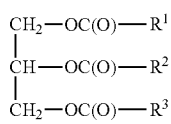

wherein;
$R^1$, $R^2$ and $R^3$ are independently selected from the group consisting of:
—$(CH_2)_e CH_3$;
$CH_3(CH_2)_7 CH=CH(CH_2)_7$—;
$CH_3$—$(CH_2)_4$—$CH=CH$—$CH_2$—$CH=CH$—$(CH_2)_7$— and mixtures thereof;
e is an integer ranging from 5 to 11.

In another preferred embodiment the liquid complex esters is a trimethylolpropane esters conforming to the following structure;

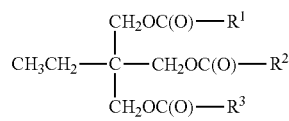

wherein;
$R^1$, $R^2$ and $R^3$ are independently selected from the group consisting of:
—$(CH_2)_e CH_3$;
$CH_3(CH_2)_7 CH=CH(CH_2)_7$—;
$CH_3$—$(CH_2)_4$—$CH=CH$—$CH_2$—$CH=CH$—$(CH_2)_7$— and mixtures thereof;
e is an integer ranging from 6 to 12.

In another preferred embodiment the liquid complex esters is a pentaerythritol esters conforming to the following structure;

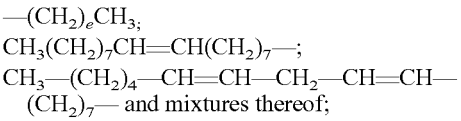

wherein;
$R^1$, $R^2$, $R^3$ and $R^4$ are independently selected from the group consisting of:
—$(CH_2)_e CH_3$;
$CH_3(CH_2)_7 CH=CH(CH_2)_7$—;
$CH_3$—$(CH_2)_4$—$CH=CH$—$CH_2$—$CH=CH$—$(CH_2)_7$— and mixtures thereof;
e is an integer ranging from 6 to 12.

In a most preferred embodiment the liquid complex esters is mixtures of glyceryl esters, trimethylolpropane esters and pentaerythritol esters.

In a preferred embodiment the % alkyl dimethicone ranges from 1 to 20% by weight. (The ester ranges from 99 to 80% respectively).

In a more preferred embodiment the % alkyl dimethicone ranges from 5 to 15% by weight. (The ester ranges from 95 to 85% respectively).

EXAMPLES

1. Alkyl Dimethicone Polymers
A. Example 1-8—Comb Polymers are available commercially from a variety of suppliers most importantly Siltech LLC in Dacula, Ga. They conform to the following structure;

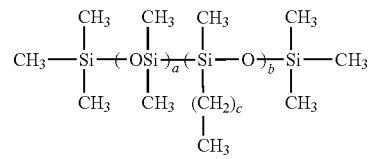

wherein:
a is an integer ranging from 0 to 200;
b is an integer ranging from 1 to 50;
c is an integer ranging from 17 to 35;

| Example | a | b | c |
|---|---|---|---|
| 1 | 0 | 1 | 17 |
| 2 | 5 | 5 | 19 |
| 3 | 10 | 7 | 19 |

-continued

| Example | a | b | c |
| --- | --- | --- | --- |
| 4 | 20 | 50 | 21 |
| 5 | 25 | 10 | 21 |
| 6 | 50 | 25 | 25 |
| 7 | 100 | 50 | 35 |
| 8 | 200 | 50 | 22 |

B. Example 9-16-Terminal alkyl dimethicone polymers are available commercially from a variety of suppliers most importantly Siltech LLC in Dacula, Ga. They conform to the following structure;

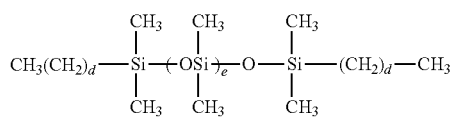

wherein:
d is an integer ranging from 17 to 35;
e in an integer ranging from 1 to 100;
and

| Example | d | e |
| --- | --- | --- |
| 9 | 17 | 1 |
| 10 | 19 | 5 |
| 11 | 21 | 10 |
| 12 | 21 | 20 |
| 13 | 35 | 50 |
| 14 | 31 | 75 |
| 15 | 17 | 25 |
| 16 | 22 | 100 |

3. Example 17-24—Mixtures of terminal and comb alkyl dimethicone

The examples 1-8 and 9-16 are mixed together and warmed until clear liquids. The admixtures are used as made.

| | Terminal | | Comb | |
| --- | --- | --- | --- | --- |
| Example | Example | Grams | Example | Grams |
| 17 | 1 | 100 | 16 | 1 |
| 18 | 2 | 100 | 15 | 5 |
| 19 | 3 | 100 | 14 | 20 |
| 20 | 4 | 100 | 13 | 50 |
| 21 | 5 | 100 | 12 | 100 |
| 22 | 6 | 100 | 11 | 500 |
| 23 | 7 | 100 | 10 | 1,000 |
| 24 | 8 | 100 | 9 | 100,000 |

4. Example 25-32—Glyceryl esters are commercially available from a variety of manufacturers including SurfaTech Corporation sold under the Cosmosurf trade name. Glyceryl esters conform to the following structure;

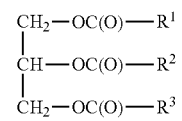

wherein;
$R^1$, $R^2$ and $R^3$ are independently selected from the group consisting of:
—$(CH_2)_e CH_3$;
$CH_3(CH_2)_7 CH=CH(CH_2)_7$—;
$CH_3$—$(CH_2)_4$—$CH=CH$—$CH_2$—$CH=CH$—$(CH_2)_7$— and mixtures thereof;
e is an integer ranging from 5 to 11;

EXAMPLES

| Example | $R^1$ | $R^2$ | $R^3$ |
| --- | --- | --- | --- |
| 25 | $CH_3(CH_2)_7CH=CH(CH_2)_7$— | —$(CH_2)_6CH_3$ | —$(CH_2)_{11}CH_3$; |
| 26 | $CH_3(CH_2)_7CH=CH(CH_2)_7$— | —$(CH_2)_7CH_3$ | —$(CH_2)_9CH_3$ |
| 27 | —$(CH_2)_7CH_3$ | —$(CH_2)_7CH_3$; | —$(CH_2)_7CH_3$ |
| 28 | —$(CH_2)_7CH_3$ | —$(CH_2)_9CH_3$ | —$(CH_2)_7CH_3$ |
| 29 | —$(CH_2)_{11}CH_3$ | —$(CH_2)_{11}CH_3$ | —$(CH_2)_9CH_3$ |
| 30 | $CH_3(CH_2)_7CH=CH(CH_2)$ | $CH_3(CH_2)_7CH=CH(CH_2)$ | $CH_3(CH_2)_7CH=CH(CH_2)$ |
| 32 | $CH_3$—$(CH_2)_4$—$CH=CH$—$CH_2$—$CH=CH$—$(CH_2)_7$— | $CH_3$—$(CH_2)_4$—$CH=CH$—$CH_2$—$CH=CH$—$(CH_2)_7$— | —$(CH_2)_{11}CH_3$ |

5. Example 33-39—Trimethylolpropane esters are commercially available from a variety of manufacturers including SurfaTech Corporation sold under the Cosmosurf trade name, and conform to the following structure conforming to the following structure;

Examples

| Example | R¹ | R² | R³ |
|---|---|---|---|
| 33 | $CH_3(CH_2)_7CH=CH(CH_2)_7-$ | $-(CH_2)_6CH_3$ | $-(CH_2)_{11}CH_3$ |
| 34 | $CH_3(CH_2)_7CH=CH(CH_2)_7-$ | $-(CH_2)_7CH_3$ | $-(CH_2)_9CH_3$; |
| 35 | $-(CH_2)_7CH_3$ | $-(CH_2)_7CH_3$; | $-(CH_2)_7CH_3$; |
| 36 | $-(CH_2)_7CH_3$ | $-(CH_2)_9CH_3$ | $-(CH_2)_7CH_3$; |
| 37 | $-(CH_2)_{11}CH_3$ | $-(CH_2)_{11}CH_3$ | $-(CH_2)_{11}CH_3$ |
| 38 | $CH_3(CH_2)_7CH=CH(CH_2)$ | $CH_3(CH_2)_7CH=CH(CH_2)$ | $CH_3(CH_2)_7CH=CH(CH_2)$ |
| 39 | $CH_3-(CH_2)_4-CH=CH-CH_2-CH=CH-(CH_2)_7-$ | $CH_3-(CH_2)_4-CH=CH-CH_2-CH=CH-(CH_2)_7-$ | $-(CH_2)_{11}CH_3$ |

6. Example 40-46—Penterythrtol esters are commercially available from a variety of manufacturers including SurfaTech Corporation sold under the Cosmosurf trade name, and conform to the following structure conforming to the following structure

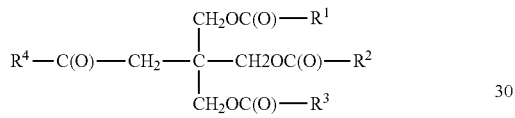

wherein;
R¹, R², R³ and R⁴ are independently selected from the group consisting of:
  $-(CH_2)_eCH_3$;
  $CH_3(CH_2)_7CH=CH(CH_2)_7-$;
  $CH_3-(CH_2)_4-CH=CH-CH_2-CH=CH-(CH_2)_7-$ and mixtures thereof;
e is an integer ranging from 6 to 12;

Examples

| Example | R¹ | R² |
|---|---|---|
| 40 | $CH_3(CH_2)_7CH=CH(CH_2)_7-$ | $-(CH_2)_6CH_3$ |
| 41 | $CH_3(CH_2)_7CH=CH(CH_2)_7-$ | $-(CH_2)_7CH_3$ |
| 42 | $-(CH_2)_7CH_3$ | $-(CH_2)_7CH_3$; |
| 43 | $-(CH_2)_7CH_3$ | $-(CH_2)_9CH_3$ |
| 44 | $-(CH_2)_{11}CH_3$ | $-(CH_2)_{11}CH$ |
| 45 | $CH_3(CH_2)_7CH=CH(CH_2)$ | $CH_3(CH_2)_7CH=CH(CH_2)$ |
| 46 | $CH_3-(CH_2)_4-CH=CH-CH_2-CH=CH-(CH_2)_7-$ | $CH_3-(CH_2)_4-CH=CH-CH_2-CH=CH-(CH_2)_7-$ |

| Example | R³ | R⁴ |
|---|---|---|
| 40 | $-(CH_2)_{11}CH_3$ | $-(CH_2)_{11}CH_3$ |
| 41 | $-(CH_2)_9CH_3$ | $-(CH_2)_{11}CH_3$ |
| 42 | $-(CH_2)_7CH_3$ | $-(CH_2)_7CH_3$ |
| 43 | $-(CH_2)_7CH_3$ | $-(CH_2)_{11}CH_3$ |
| 44 | $-(CH_2)_7CH_3$ | $-(CH_2)_{11}CH_3$ |
| 45 | $CH_3(CH_2)_7CH=CH(CH_2)$ | $-(CH_2)_{11}CH_3$ |
| 46 | $-(CH_2)_{11}CH_3$ | $-(CH_2)_{11}CH_3$ |

7. Example 47-54—Mixtures of glyceryl esters, trimethylolpropane esters, and pentaerythritol esters.

Examples

|  | Glyceryl Ester | | Trimethylolpropane Ester | | Pentaerythritol Ester | |
|---|---|---|---|---|---|---|
| Example | Example | Grams | Example | Grams | Example | Grams |
| 47 | 25 | 0 | 33 | 10 | 40 | 100 |
| 48 | 26 | 100 | 34 | 5 | 41 | 50 |
| 49 | 27 | 100 | 35 | 1 | 44 | 50 |
| 50 | 28 | 100 | 36 | 100 | 43 | 100 |
| 51 | 29 | 100 | 37 | 500 | 44 | 1 |
| 52 | 30 | 100 | 38 | 1000 | 45 | 0 |
| 53 | 31 | 100 | 39 | 500 | 46 | 1 |
| 54 | 32 | 100 | 33 | 0 | 40 | 50 |

Products of the Present Invention

To the specified number of grams of the specified ester is added the specified number of grams of the specified alkyl dimethicone. The mixture is heated to 80° C., until clear. The mixture is agitated 30 minutes then cooled. The structured gel is formed as the mixture cools. Optional additives are added while hot.

|  | Alkyl Dimethicone | | Ester | |
|---|---|---|---|---|
| Example | Example | Grams | Example | Grams |
| 55 | 1 | 1 | 17 | 99 |
| 56 | 2 | 5 | 18 | 95 |
| 57 | 3 | 10 | 19 | 90 |
| 58 | 4 | 15 | 20 | 85 |
| 59 | 5 | 20 | 21 | 80 |
| 60 | 6 | 1 | 22 | 99 |
| 61 | 7 | 5 | 23 | 95 |
| 62 | 8 | 10 | 24 | 90 |
| 63 | 9 | 15 | 25 | 85 |
| 64 | 10 | 20 | 26 | 80 |
| 65 | 11 | 1 | 27 | 99 |
| 66 | 12 | 2 | 28 | 98 |
| 67 | 13 | 5 | 29 | 95 |
| 68 | 14 | 10 | 30 | 90 |
| 69 | 15 | 15 | 31 | 85 |
| 70 | 16 | 20 | 32 | 80 |
| 71 | 16 | 1 | 33 | 99 |
| 72 | 15 | 3 | 34 | 97 |
| 73 | 14 | 7 | 35 | 93 |
| 74 | 13 | 12 | 36 | 88 |
| 75 | 12 | 15 | 37 | 85 |
| 76 | 11 | 18 | 38 | 89 |
| 77 | 10 | 20 | 39 | 80 |
| 78 | 9 | 1 | 40 | 99 |
| 79 | 8 | 5 | 41 | 95 |
| 80 | 7 | 10 | 42 | 90 |
| 81 | 6 | 15 | 43 | 85 |
| 82 | 5 | 20 | 44 | 80 |
| 83 | 4 | 1 | 45 | 99 |
| 84 | 3 | 5 | 46 | 95 |
| 85 | 2 | 8 | 47 | 92 |
| 86 | 1 | 11 | 48 | 89 |
| 87 | 1 | 15 | 49 | 85 |
| 88 | 2 | 20 | 50 | 80 |
| 89 | 3 | 20 | 51 | 80 |
| 90 | 4 | 18 | 52 | 82 |
| 91 | 5 | 15 | 53 | 85 |
| 92 | 4 | 5 | 54 | 95 |

Applications Examples

The compositions of the present invention are structured gels. The lower percentages of alkyl alkyl dimethicone (1-5% by weight) are soft gels. They liquefy upon the touch and spread rapidly on the skin. At ranges of between 5 and 10% by weight added alkyl dimethicone, the structured gels are rigid but still yield under pressure. The cushion is better. By cushion is meant the thickness of the liquid under the finger while spreading. The amount of time necessary to spread out the composition is the play time. The intermediate level of between 5 and 10% by weight have short play times, spreading out rapidly. At levels of between 10 and 20% by weight the gel is very rigid and the play time is extended. This allows the formulation of products that have wide cosmetic applications, allowing the formulator wide latitude to develop a product that meets consumer expectations.

The higher the number of carbon atoms in the alkyl dimethicone, the higher the melting point of the structured gel. At the melt point the structured gel dissolves making a liquid, upon cooling the structured gel reforms, making the technology very flexible.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A structured gel composition comprising
  (a) an alkyl dimethicone polymer selected from the group consisting of:
    i. a comb branched alkyl dimethicone polymer conforming to the following structure;

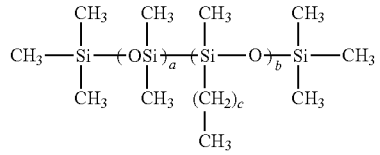

wherein:
    a is an integer ranging from 0 to 200;
    b is an integer ranging from 1 to 50;
    c is an integer ranging from 17 to 35;
    ii. a terminal alkyl dimethicone polymer conforming to the following structure;

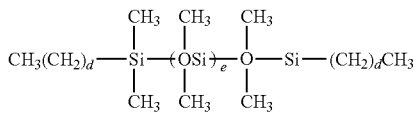

wherein:
    d is an integer ranging from 17 to 35;
    e in an integer ranging from 1 to 100;
    and iii. mixtures thereof;
said alkyl dimethicone polymers having a melting point of above 30° C., and
(b) a liquid complex esters selected from the group consisting of
  i. glyceryl esters conforming to the following structure;

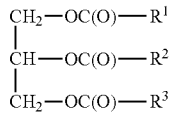

wherein;
$R^1$, $R^2$ and $R^3$ are independently selected from the group consisting of:
—$(CH_2)_e CH_3$;
$CH_3(CH_2)_7 CH=CH(CH_2)_7$—;
$CH_3$—$(CH_2)_4$—$CH=CH$—$CH_2$—$CH=CH$—$(CH_2)_7$— and mixtures thereof;
e is an integer ranging from 5 to 11;
  ii. trimethylolpropane esters conforming to the following structure;

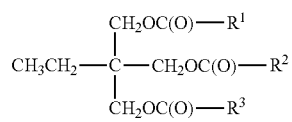

wherein;
$R^1$, $R^2$ and $R^3$ are independently selected from the group consisting of:
—$(CH_2)_e CH_3$;
$CH_3(CH_2)_7 CH=CH(CH_2)_7$—;
$CH_3$—$(CH_2)_4$—$CH=CH$—$CH_2$—$CH=CH$—$(CH_2)_7$— and mixtures thereof;
e is an integer ranging from 6 to 12;
and
  iii. pentaerythritol esters conforming to the following structure;

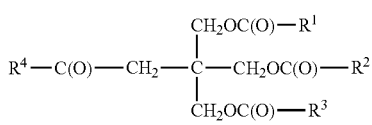

wherein;
$R^1$, $R^2$, $R^3$ and $R^4$ are independently selected from the group consisting of:
—$(CH_2)_e CH_3$;
$CH_3(CH_2)_7 CH=CH(CH_2)_7$—;
$CH_3$—$(CH_2)_4$—$CH=CH$—$CH_2$—$CH=CH$—$(CH_2)_7$— and mixtures thereof;
e is an integer ranging from 6 to 12;
  iv. and mixtures thereof;
wherein said esters have melting points of below 25° C.

2. A structured gel of claim 1 wherein the alkyl dimethicone polymer is a comb branched alkyl dimethicone polymer conforming to the following structure;

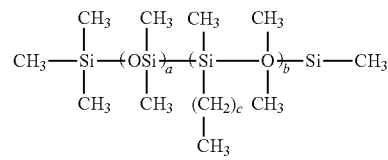

wherein:
a is an integer ranging from 0 to 200;
b is an integer ranging from 1 to 50;
c is an integer ranging from 17 to 35.

3. A structured gel of claim 1 wherein the alkyl dimethicone polymer is a terminal alkyl dimethicone polymer conforming to the following structure;

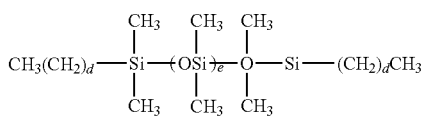

wherein:
d is an integer ranging from 17 to 35;
e in an integer ranging from 1 to 100.

4. A structured gel of claim 1 wherein the liquid complex esters is a glyceryl ester conforming to the following structure;

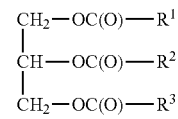

wherein;
$R^1$, $R^2$ and $R^3$ are independently selected from the group consisting of:
—$(CH_2)_e CH_3$;
$CH_3(CH_2)_7 CH=CH(CH_2)_7$—;
$CH_3$—$(CH_2)_4$—$CH=CH$—$CH_2$—$CH=CH$—$(CH_2)_7$— and mixtures thereof;
e is an integer ranging from 5 to 11.

5. A structured gel of claim 1 wherein the liquid complex esters is a trimethylolpropane esters conforming to the following structure;

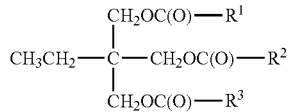

wherein;
$R^1$, $R^2$ and $R^3$ are independently selected from the group consisting of:
—$(CH_2)_e CH_3$;
$CH_3(CH_2)_7 CH=CH(CH_2)_7$—;
$CH_3$—$(CH_2)_4$—$CH=CH$—$CH_2$—$CH=CH$—$(CH_2)_7$— and mixtures thereof;
e is an integer ranging from 6 to 12.

6. A structured gel of claim 1 wherein the liquid complex esters is a pentaerythritol esters conforming to the following structure;

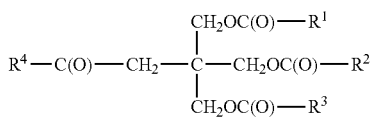

wherein;
$R^1$, $R^2$, $R^3$ and $R^4$ are independently selected from the group consisting of:
—$(CH_2)_e CH_3$;
$CH_3(CH_2)_7CH=CH(CH_2)_7$—;
$CH_3$—$(CH_2)_4$—CH=CH—$CH_2$—CH=CH—$(CH_2)_7$— and mixtures thereof;
e is an integer ranging from 6 to 12.

7. A structured gel of claim 1 wherein the liquid complex esters is mixtures of glyceryl esters, trimethylolpropane esters and pentaerythritol esters.

8. A structured gel of claim 1 wherein the percentage of alkyl dimethicone ranges from 1 to 20% by weight.

9. A structured gel of claim 1 wherein the percentage of alkyl dimethicone ranges from 5 to 15% by weight.

10. A process for treating skin with a structured gel composition comprising contacting the skin with an effective conditioning concentration of a composition which comprises;

(a) an alkyl dimethicone polymer selected from the group consisting of
    i. a comb branched alkyl dimethicone polymer conforming to the following structure;

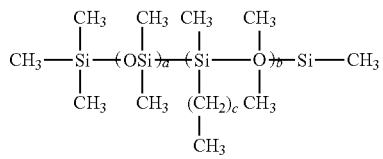

wherein:
    a is an integer ranging from 0 to 200;
    b is an integer ranging from 1 to 50;
    c is an integer ranging from 17 to 35;
    ii. a terminal alkyl dimethicone polymer conforming to the following structure;

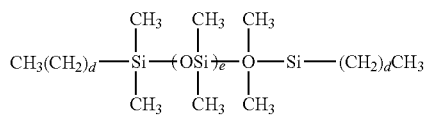

wherein:
    d is an integer ranging from 17 to 35;
    e in an integer ranging from 1 to 100;
    and
    iii. mixtures thereof;
    said alkyl dimethicone polymers having a melting point of above 30° C., and (b) a liquid complex esters selected from the group consisting of
i. glyceryl esters conforming to the following structure;

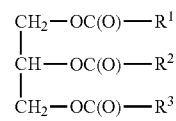

wherein;
$R^1$, $R^2$ and $R^3$ are independently selected from the group consisting of:
—$(CH_2)_e CH_3$;
$CH_3(CH_2)_7CH=CH(CH_2)_7$—;
$CH_3$—$(CH_2)_4$—CH=CH—$CH_2$—CH=CH—$(CH_2)_7$— and mixtures thereof;
e is an integer ranging from 5 to 11;

ii. trimethylolpropane esters conforming to the following structure

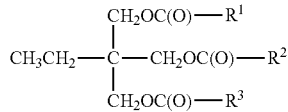

wherein;
$R^1$, $R^2$ and $R^3$ are independently selected from the group consisting of:
—$(CH_2)_e CH_3$;
$CH_3(CH_2)_7CH=CH(CH_2)_7$—;
$CH_3$—$(CH_2)_4$—CH=CH—$CH_2$—CH=CH—$(CH_2)_7$— and mixtures thereof;
e is an integer ranging from 6 to 12;
and iii. pentaerythritol esters conforming to the following structure;

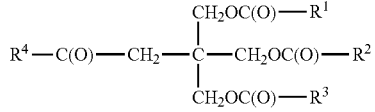

wherein;
$R^1$, $R^2$, $R^3$ and $R^4$ are independently selected from the group consisting of:
—$(CH_2)_e CH_3$;
$CH_3(CH_2)_7CH=CH(CH_2)_7$—;
$CH_3$—$(CH_2)_4$—CH=CH—$CH_2$—CH=CH—$(CH_2)_7$— and mixtures thereof;
e is an integer ranging from 6 to 12;

iv. and mixtures thereof;
wherein said esters have melting points of below 25° C.
and (c) optionally sun screen actives, hydroxy acids, antioxidants, flavonoids, tocopherol, and vitamins.

11. A process of claim 10 wherein said effective conditioning concentration ranges from 0.1% to 25% by weight of the composition.

12. A process of clam 10 wherein the alkyl dimethicone polymer is a comb branched alkyl dimethicone polymer conforming to the following structure;

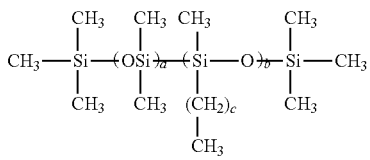

wherein:
a is an integer ranging from 0 to 200;
b is an integer ranging from 1 to 50;
c is an integer ranging from 17 to 35.

13. A process of claim 10 wherein the alkyl dimethicone polymer is a terminal alkyl dimethicone polymer conforming to the following structure;

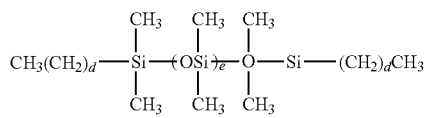

wherein:
d is an integer ranging from 17 to 35;
e in an integer ranging from 1 to 100.

14. A process of claim 10 wherein the complex esters is a glyceryl ester conforming to the following structure;

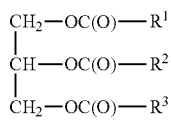

wherein;
$R^1$, $R^2$ and $R^3$ are independently selected from the group consisting of:
—$(CH_2)_e CH_3$;
$CH_3(CH_2)_7 CH\!\!=\!\!CH(CH_2)_7$—;
$CH_3$—$(CH_2)_4$—$CH\!\!=\!\!CH$—$CH_2$—$CH\!\!=\!\!CH$—$(CH_2)_7$— and mixtures thereof;
e is an integer ranging from 5 to 11.

15. A process of claim 10 wherein the complex esters is a trimethylolpropane esters conforming to the following structure;

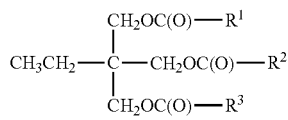

wherein;
$R^1$, $R^2$ and $R^3$ are independently selected ram the group consisting of:
—$(CH_2)_e CH_3$;
$CH_3(CH_2)_7 CH\!\!=\!\!CH(CH_2)_7$—;
$CH_3$—$(CH_2)_4$—$CH\!\!=\!\!CH$—$CH_2$—$CH\!\!=\!\!CH$—$(CH_2)_7$— and mixtures thereof;
e is an integer ranging from 6 to 12.

16. A process of claim 10 wherein the liquid complex esters is a pentaerythritol esters conforming to the following structure;

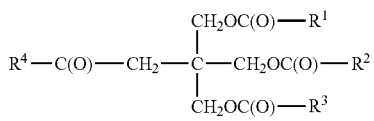

wherein;
$R^1$, $R^2$, $R^3$ and $R^4$ are independently selected from the group consisting of:
—$(CH_2)_e CH_3$;
$CH_3(CH_2)_7 CH\!\!=\!\!CH(CH_2)_7$—;
$CH_3$—$(CH_2)_4$—$CH\!\!=\!\!CH$—$CH_2$—$CH\!\!=\!\!CH$—$(CH_2)_7$— and mixtures thereof;
e is an integer ranging from 6 to 12.

17. A process of claim 10 wherein the liquid complex esters is mixtures of glyceryl esters, trimethylolpropane esters and pentaerythritol esters.

18. A process of claim 10 wherein the percentage of alkyl dimethicone ranges from 1 to 20% by weight.

19. A process of claim 10 wherein the percentage of alkyl dimethicone ranges from 5 to 15% by weight.

* * * * *